United States Patent [19]

Sher et al.

[11] Patent Number: 5,341,692
[45] Date of Patent: Aug. 30, 1994

[54] DEVICE FOR TAKING, PRESERVING AND TRANSPORTING A FLUID SAMPLE FOR ANALYSIS

[75] Inventors: Samuel E. Sher, Rockaway; Stephen A. Borgianini, Mount Holly; Robert E. Carpenter, Nutley; Scott Santora, Hammonton; William S. Scavuzzo, Clark, all of N.J.

[73] Assignee: Norton Company, Worcester, Mass.

[21] Appl. No.: 792,324

[22] Filed: Nov. 12, 1991

[51] Int. Cl.⁵ .............................................. G01N 1/12
[52] U.S. Cl. .................... 73/864.63; 73/864.64; 73/864.91; 73/864.51
[58] Field of Search ............ 73/864.63, 864.64, 864.67, 73/864.91, 863.8, 863.84, 863.85, 864.34, 864.35, 864.51, 864.62, 864.86

[56] References Cited

U.S. PATENT DOCUMENTS

| | | | |
|---|---|---|---|
| 2,059,999 | 11/1936 | Rainville, Sr. | 137/18 |
| 2,625,226 | 1/1953 | Wofford | 73/864.63 |
| 3,886,800 | 6/1975 | Boehringer | 73/241.5 |
| 4,346,519 | 8/1982 | Milo | 73/864.63 |
| 4,546,659 | 10/1985 | Gill et al. | 73/864.52 |
| 4,625,574 | 12/1986 | Robbins | 73/864.63 |
| 4,799,389 | 1/1989 | Krauss et al. | 73/864.53 |
| 5,139,654 | 8/1992 | Carpenter | 73/864.63 |

Primary Examiner—Hezron E. Williams
Assistant Examiner—Nashmiya Ashraf
Attorney, Agent, or Firm—Brian M. Kolkowski

[57] ABSTRACT

A device made of non-contaminating inert material for taking and preserving a fluid sample containing volatile substances for analysis having a tubular body with gas tight valves at opposite end portions which are opened to allow fluid to pass into and out of a chamber and closed to seal off the escape of and preserve a fluid sample therein during transfer to a laboratory for analysis. Opposite end portions of the tubular body are adapted for attachment of a lower one-way inlet check valve unit and an upper outlet extension unit thereto used with a supporting line or rod to lower and raise the device into and out of a body of fluid and thereby take a fluid sample thereof for analysis. Closing of the valves traps fluid and seals off the sample taken into the chamber between the valves and is removed therefrom by piercing a septum located adjacent the chamber and between the valves by suitable means including a hypodermic needle.

15 Claims, 2 Drawing Sheets

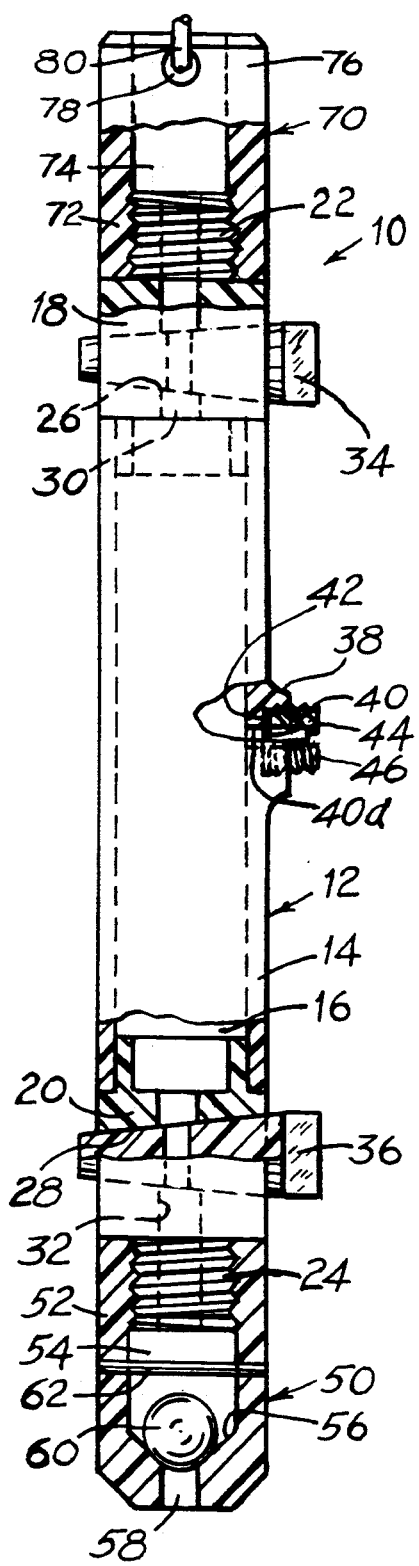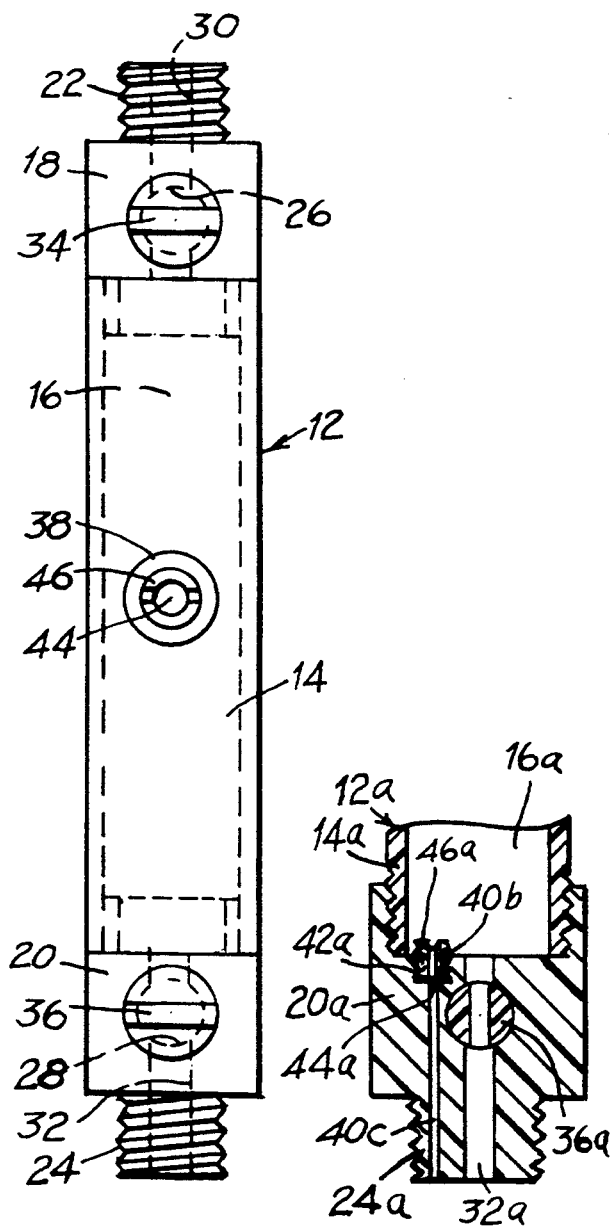
Fig.1　Fig.2　Fig.3

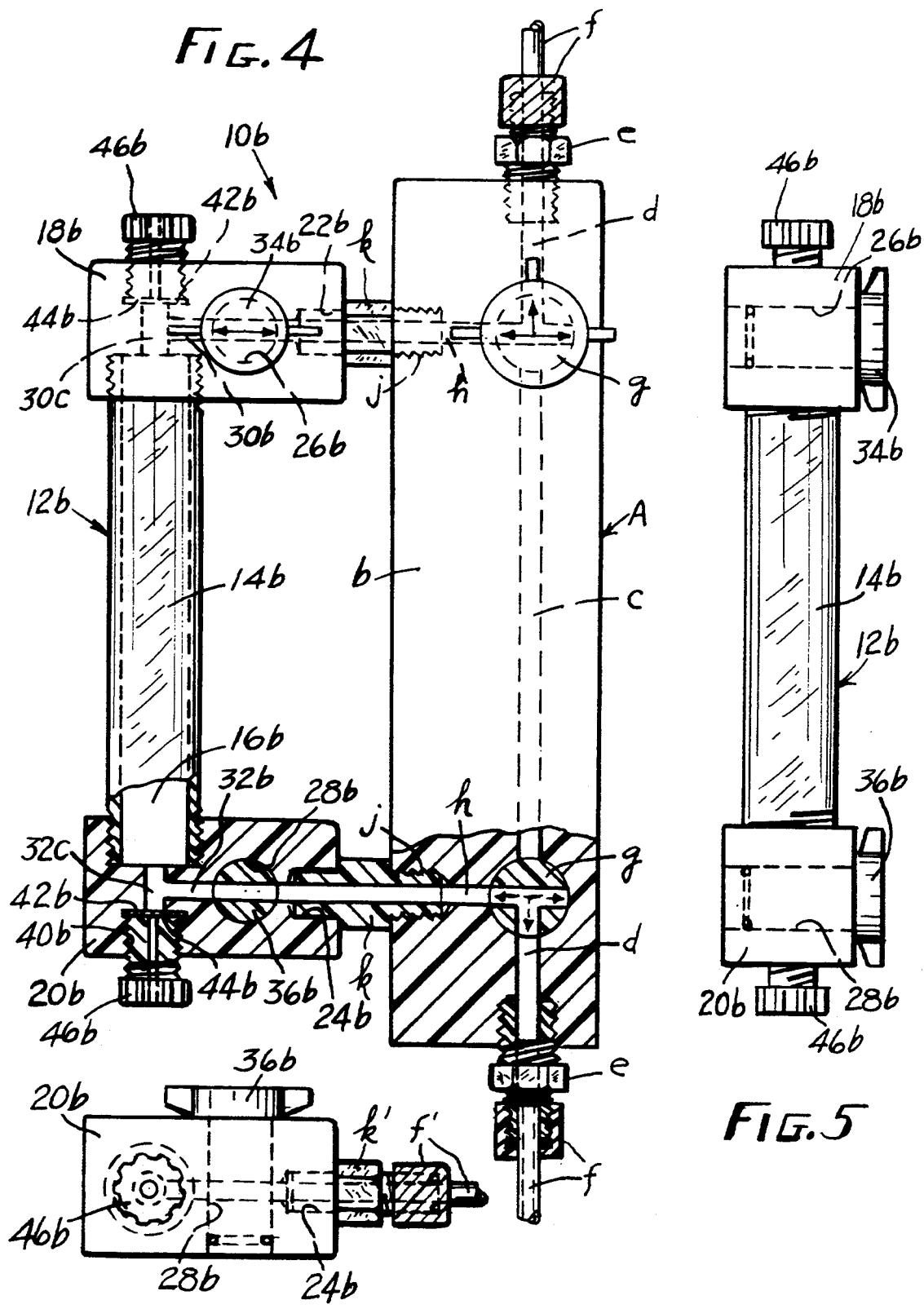

DEVICE FOR TAKING, PRESERVING AND TRANSPORTING A FLUID SAMPLE FOR ANALYSIS

TECHNICAL DISCLOSURE

A device made of inert non-contaminating materials for taking and preserving a fluid sample taken from a body such as water and any volatiles contained therein during transportation from the test site to the laboratory for analysis.

BACKGROUND OF THE INVENTION

1. Field of the Invention

The invention relates to devices for taking a sample from various bodies of fluids such as water from underground wells, tanks, barrels, and reservoirs and sealing the contents thereof against any loss or addition of volatile substances and contaminates during transfer to a laboratory for analysis.

2. Description of the Prior Art

Heretofore samples of a body of fluid/liquid such as water to be analyzed for contamination and volatile substances has been obtained by lowering a vessel such as a bailer into the body of liquid to be tested. When filled, the bailer containing the sample is withdrawn to the surface whereupon a valve at one or both bottom and top ends close to contain the liquid therein. One such sampling device which seals off the upper and lower ends thereof is disclosed in U.S. Pat. No. 2,059,999.

Another known device which seals a liquid sample between a septum cap later screwed onto its upper end and a lower ball check valve is disclosed in U.S. Pat. No. 4,625,574.

Still another device for obtaining and transferring a gas sample for analysis has a septum pierceable by a hypodermic needle sealing off the lower exit end thereof is shown in U.S. Pat. No. 3,886,800. However, unlike the applicant's device, the prior art device allows possible opening of the check valves and thus addition or escape of gases or volatile substances which may be present in the fluid sample during handling and preparation of the device for transfer to another container and to the laboratory for analysis.

The applicant's device differs from the prior art in that no transfer of the fluid sample to another container takes place. The applicant's device has means for taking and positively preserving the fluid sample and preventing the escape of any of the constituents of the sample including gases and volatiles during, taking, handling, and transfer of the fluid sample for analysis.

SUMMARY OF THE INVENTION

A fluid sampling device adapted for taking and preserving a fluid sample during transfer to the laboratory for analysis is made of inert non-contaminating materials and has a main tubular body including an outer wall extending around an inner central fluid sample receiving and retaining chamber situated between and sealingly attached to opposite inlet and outlet end portions.

Each of the end portions has fastening means such as a threaded portion for making attachments thereto, an internal fluid passage extending to and from the inner chamber and a gas tight valve to close each of the internal fluid passages. A removable one way check valve unit is attachable to the lower inlet end portion and a removable outlet extension unit for receiving fluid overflow and means for lowering and raising the sampling device into and out of a body of fluid is attachable to the upper outlet end portion.

Means including a self sealable septum located in an access passage connected to and adjacent the inner chamber and between manually closed gas tight valves at opposite ends of the tubular body act together to seal off the fluid sample in the inner chamber and thereby positively preserve the constituents thereof and prevent entrance of or escape of any volatile or gaseous matter contained therein.

Thus, the sealed fluid sample obtained at a given depth of a body of fluid can be transported to a laboratory for analysis, after closing of the valves and removal of the upper outlet extension and lower check valve units from the tubular body. At the laboratory the sample may be withdrawn from the inner chamber by piercing the sealable septum with the hypodermic needle of any suitable device such as a sealed hypodermic syringe. Hence, it is seen that the device takes, seals, and transfers a fluid sample without ever exposing the fluid sample to the atmosphere or any other contaminants.

DESCRIPTION OF THE DRAWINGS

FIG. 1 is a view partly in cross-section of the sampling device assembled together and adapted for lowering into a body of fluid such as water and to take a sample thereof at any desired depth;

FIG. 2 is a view of the sampling device adapted to preserve the fluid sample sealed therein by the closing of the valves and removing of the outer extension and lower inlet valve units thereof and for transfer of the field sample to a testing laboratory for analysis;

FIG. 3 is a partial view in section of another embodiment of the invention wherein the septum is located in an end portion sealingly attached to one end of a tubular body enclosing the inner-chamber;

FIG. 4 is a view of another embodiment of a sampling device adaptable for use with a pumping unit and which is easily connected to and disconnected from a pumping unit adapter;

FIG. 5 is a left hand side view of the sampling device of FIG. 4 disconnected from the pumping unit adapter; and FIG. 6 is a bottom end view of the sampling device of FIG. 4 disconnected from the pumping unit adapter.

DESCRIPTION OF THE PREFERRED EMBODIMENT(S)

Referring to FIG. 1, a fluid sample taking, sealing, and transfer device 10 comprises a main elongated tubular body or cell unit 12 having an outer wall 14 surrounding a relatively large inner chamber 16 therein extending to and sealingly attached to opposite upper outlet and lower inlet end portions or valve bodies 18 and 20. The opposite end portions or valve bodies 18 and 20 have fastening means such as externally threaded end portions 22 and 24 extending from each of the ends. The valve bodies 18 and 20 also contain gas-tight valve portions including preferably tapered valve bores 26 and 28 extending crosswise therein. Fluid inlet and outlet passages 30 and 32 extend axially from ends and through the threaded end portions 22 and 24 into communication with the valve bores 26 and 28 and the internal fluid receiving chamber 16.

A pair of preferably tapered gas tight valves, valve stems, or stopcocks 34 and 36 are provided for sealing and mating engagement with the internal surfaces of the tapered bores 26 and 28. The stopcocks or valve stems 34 and 36 have valve passages therein and outer ends or heads that have either an elongated slot, handle or flat surfaces thereon which may be aligned with the passages 30 and 32 to indicate direction of the valve passage therein and allow passage of fluid therethrough or turned or rotated out of alignment to stop and prevent passage of fluid therethrough. Opened by turning of the tapered stopcocks 34 and 36 so that the elongated handles are aligned with the elongated axis of the main body 12 allows flow through the inlet and outlet passages and turning the valve handles crosswise or perpendicular to the axis closes the tapered stopcocks and prevents passage of fluid through the passages 30 and 32.

In the outer wall of the tubular main body are seal means including a boss 38 through which extends an internally threaded step or counter bore 40 extending to a shoulder 42 and on through a smaller access bore 40a in communication with the chamber 16. A self resealable septum type diaphragm 44 is held in place against the shoulder 42 by an externally threaded hollow or tubular retainer 46 and seals off the access bore 40a and prevents escape from the chamber 16 of any of the contaminants of a sample contained therein. However, the resealable septum 44 is provided whereby a hypodermic needle and syringe or any other suitable device may be utilized by laboratory testing personnel to pierce the septum and draw a sample of the fluid from the chamber 16 for analysis.

In order to take and preserve a sample of fluid taken at a prescribed depth in a body thereof, the sampling device 10 is preferably provided at one lower threaded end portion 24 with an inlet one way check valve unit or adapter 50. The inlet check valve unit 50 has an internally threaded upper end portion 52 adapted to be threaded to lower end portion 24 of the main tubular cell or body 12. A valve chamber 54 extends internally from the threaded portion 52 to a beveled check valve seat 56 situated adjacent the lower entrance or inlet end passage 58 which maybe opened or closed off by engagement of a ball check valve 60. The inlet valve unit 50 also has a pin or stop 62 extending through the chamber 54 whereby the ball check valve 60 may be raised a limited amount by the incoming fluid sample and thus prevent the ball from obstructing the inlet passage 32 and flow of fluid into the chamber 16.

At the opposite upper outlet end portion 22 of the main body or cell 12 is threadably attached an upper or outlet extension unit 70 that is similar to a standard bailer and by which the sampling device may be lowered into and raised from a body of fluid to be tested and contain overflow of fluid or liquid above the chamber 16.

The outlet extension unit 70 comprises a tubular internally threaded portion 72 threaded at its lower end onto the threaded portion 22 and extends upwardly around a central fluid overflow receiving passage 74 to a vented or open upper outlet end portion 76 through the outer wall of which a bore 78 extends for attaching a line or rod 80 for lowering and raising the assembled device 10.

With the exception of the septum 44 and the line or rod 80, the various parts of the sampling device described herein above may be made of any suitable non-contaminating inert plastic, ceramic or metallic materials, for example, polyvinylchloride (PVC), polyethylene, glass, alumina and stainless steel or any mixture thereof. Preferably they are made of 100% virgin fluorocarbon materials such as polytetrafluoroethylene (PTFE) and fluorinated ethylene propylene polymer (FEP).

The septum diaphragm 44 may be made of any suitable resilient, self sealing, non-contaminating elastomeric material well known in the art, including teflon laminate.

Optionally the main tubular body 12 may be fabricated entirely of or only the outer wall or tube 14 between the opposite inlet and outlet end portions thereof made of transparent or translucent non-contaminating inert material. Thus, the fluid sample sealed within the chamber 16 would be visible to the naked eye.

Another variation or embodiment of the sampling device 10 is to provide the main tubular body 12 with a septum located in either or both the inlet or outlet end portions instead of in the outer wall portion 14 as shown in FIG. 1.

Preferably the sampler device 10 would then have, as shown in FIG. 3, a tubular main body 12a including an outer wall 14a extending from the outlet end portion 18 and sealingly attached or threaded to an inlet end portion or valve body 20a. The lower inlet end portion or valve body 20a would then preferably have an internally threaded counter bore 40b, an access bore 40c, and an annular shoulder 42a situated adjacent a gastight valve stem 36a and a fluid passage 32a therein. A resealable septum 44a is held in place and sealed against the shoulder 42a by an externally threaded tubular retainer 46a and thereby seals off the smaller access bore 40c to the inner chamber 16a and prevents escape of any of the fluid sample sealed within the adjacent chamber 16b.

Thus as before, the septum 44a is still located adjacent the inner chamber 16a and in between the gas tight valves 34 and 36a and is pierceable by inserting a hypodermic needle through the access bore 40c after removal of an inlet check valve unit therefrom.

The sampling device described hereinabove may be utilized to take and preserve a fluid sample as follows: the device 10 is assembled as shown in FIG. 1 with the upper outlet extension unit 70 and lower inlet check valve unit 50 attached to the main tubular body 12. A line or rod 80 is attached to the upper extension 70 and the valves 34 and 36 are opened to allow fluid to pass into and through the chamber 16. Sampling device 10 is then lowered into a body of fluid to the depth where the sample is to be taken. During its decent, the ball check valve 60 is lifted off its seat and is arrested by stop pin 62 whereupon fluid enters inlet passage 58, raises ball check 60 off its seat 56 and allows fluid to flow through inlet passage 32, valve 36, into and through chamber 16, out through valve 34 outlet passage 30, and overflow into and out the outlet extension 70. Air above the fluid entering the device is forced out the chamber 16 and vented from the device by means of the vent opening 76 in the outlet extension unit. After a few minutes, the device 10 completely vented and filled with a fluid sample taken at the desired depth is raised by means of the line 80. During its ascent and reverse movement to the surface, the check valve 60 is forced by the fluid therein against the valve seat 56 and closes the check valve and thereby traps the fluid sample therein. At the surface the gas tight valves 34 and 36 are closed while holding the device vertically and with the level of fluid overflow extending well into the outlet extension. Once the valves are closed the excess fluid overflow in the outlet extension may be, if desired, poured into another container for analysis other than those concerned with volatile substances. Both the extension 70 and check valve units 50 are removed from the main body 12 containing the fluid sample sealed therein. The main body 12 or 12a and fluid sample sealed therein is then transported to a laboratory for analysis. A suitable sealed device such as a syringe with attached hypodermic needle may then be used to sealingly pierce the septum 44 or 44a and sealingly withdraw without exposure to the atmosphere, fluid from the chambers 16 or 16a for analysis.

If desired, the device may be connected to various adapters and to other devices such as a-well known bailer and one or more of the devices described hereinabove may be connected together and thereby adapted to take more than one fluid sample from the same body. A fluid sample may also be taken with the device described hereinabove without attaching the check valve unit 50 and/or the outlet extension unit 70 thereto. The tubular body 12 with the attached valves 34 and 36 open would be lowered into the body of fluid by hand and when filled, the valve 34 and 36 are closed while the device is held submerged beneath the surface of the fluid. Thus the chamber 16 is filled with a sample and sealed for transfer to a laboratory for analysis.

Although the valves 34 and 36 are shown to be tapered, they may be made cylindrical and fitted tightly to the valve bore to provide a gastight seal. Instead of being rotary valves they may be made to move axially to open and close the inlet and outlet passages.

End portions 18 and 20 may be made as integral parts of the tubular body 12 and/or as part of gas tight valve bodies and sealingly attached to the outer wall 14 of the tubular body 12. As shown in FIG. 3, they may be threaded together or force fitted together as shown in FIG. 1 and if desired, be cemented together.

Where access to a body of fluid to be analyzed is limited and the device described hereinabove cannot be submerged therein, it may be connected to an inline non-contaminating pumping unit including a tubular conduit. The outlet end of the inert tubing including an adapter or nut could be connected to either of the inlet ends 24 of the device or inlet 58 of unit 50 and the opposite inlet end connected to the outlet end of a hand pump. A flexible tubular conduit of sufficient length connected to the inlet end of the pump could then be inserted through a small opening of limited size and to the desired depth in the body of fluid to be analyzed. Hence, the fluid can be pumped into and through the device until it overflows the outlet end 76 whereupon the valves 36 and 34 are closed to seal a sample of the fluid in the chamber 16 for analysis as taught hereinabove.

Still another embodiment of a sampling device of the invention that is specifically adapted for connection to and use with a pumping system is shown in FIGS. 4, 5, and 6. The sampling device 10b shown in FIG. 4 comprises a main elongated tubular body or cell unit 12b having an outer wall 14b surrounding an inner chamber 16b and extending between end portions threaded into or sealingly connected to opposite upper outlet and lower inlet end portions or valve bodies 18b and 20b. Each of the valve bodies or end portions 18b and 20b are substantially identical in construction and have fastening means such as the surfaces of the counter bores 22b and 24b extending inwardly from and about the inlet and outlet sides of the respective valve bodies 18b and 20b. Gas tight valve means including bores 26b and 28b extend crosswise through the valve bodies 18b and 20b and at right angles to fluid inlet and outlet passages 30b and 32b extending from the inlet and outlet counter bores 22b and 24b and through the end portions 18b and 20b into communication with the internal fluid receiving inner chamber 16b.

A pair of gas tight valves, valve stems, or stopcocks 34b and 36b are provided for sealing mating engagement with the internal surface of the bores 26b and 28b and have valve passages therein and outer heads with either elongated slotts, handles, or flat surfaces thereon which may be aligned with the passages 30b and 32b to indicate the direction of the valve passage therein and allow fluid to flow through and which can be rotated out of alignment to prevent fluid passage therethrough and into or escape of fluid from the inner chamber 16b.

At least one but preferably each of the inlet and outlet end portions or valve bodies 18b and 20b have internally threaded counter bores 40b extending inwardly to an annular shoulder 42b situated adjacent each of the gas tight valve means 36b and 34b and passages 30b and 32b. A resealable septum 44b is held in place and sealed against the annular shoulders 42b by an externally threaded tubular retainer 46b which seals off access to passages 30c and 32c adjacent inner chamber 16b and prevents escape of the sealed fluid sample therefrom prior to analysis. Each of the septums 44b located adjacent the inner chamber 16b are still situated in between the gastight valves 34b and 36b and each is piercable by inserting a hypodermic needle through the tubular retainer 46b and withdrawing a fluid sample from the inner chamber 16b.

The sampling device 12b is adapted as a unit to be connected either directly to flexible conduits attached to a pumping device or by way of a pumping unit adapter A interposed between the pump and the sampling device.

As shown, the pumping unit adapter A comprises an elongated manifold valve block b with an internal bypass passage C extending between valves g and connectable to an upper outlet and lower inlet passage d, each of which is attached to a tube fitting e connected to the manifold and to tubular flexible conduits f. One of the conduits f is connectable to a pump connectable by a similar conduit to a body of fluid from which a sample is to be taken. The attached upper conduit may be omitted, if desired, or preferably connected to another container into which fluid can be pumped or allowed to overflow into.

A gastight valve g is provided in each of the opposite end portions of the manifold block b for the purpose of selectively allowing pumped fluid to bypass directly through the block b or to divert the flow of fluid into and through the inner chamber 16b of the sampling device 12b attached to the manifold b of adapter A. Each valve g has a T-shaped passage in a valve stem and is rotatable by means such as T-shaped handles or slots aligned with the T-shaped passage in the valve stem for the purpose of indicating the position of the T-shaped passage in relation to the passage C and the internal fluid inlet and outlet passages d and h within each end portion of the block b. Each of the passages h extends from each of the valves g to an internally threaded bore j into which is threaded a tubular connector or tube fitting having an annular end portion extending from a side of the manifold b and plugged into gastight sealing engagement with surfaces about the bores 22b and 24b adjacent the inlet and outlet sides of the end portions or valve bodies 18*b* and 20*b* of the sampling device 12*b*. Hence the sampling device 12*b* is easily connected to and disconnected from the pumping adapter A and manifold block b by manually pushing them together or pulling them apart.

Thus, to take and seal a fluid sample by use of a pumping device and the adapter A, the valves g are rotated so that the T-shaped passages therein are aligned to close off the bypass passage C between the valves g and direct fluid pumped by the pump through the valves g into and out of passages h. The sampling device is then pushed onto the tubular connectors k projecting from the manifold b of adapter A. Both valves 34*b* and 36*b* are rotated to the open position which allows passage of the fluid sample pumped, to pass through inlet passages 32*b*, 32*c*, into the inner chamber 16*b* and out passage 30*c*, 30*b* through valve 34*b*, upper passage h through upper outlet valve g passage d and out conduit f. When fluid over flows out conduit f valves 34*b* and 36*b* are closed to seal the fluid sample within the inner chamber 16*b*. Valves g may then be rotated out of alignment with and close off passage h and into alignment with bypass passages c and d for further pumping of fluid into another container for different analysis or purposes. With valves 34*b* and 36*b* closed the sampling device 12*b* can be pulled away and disconnected from the adapter A manifold block b and transferred with the sample sealed therein to a laboratory for analysis as taught hereinabove.

Alternatively the sampling device 12*b* may be connected directly to a pumping device without the use of the adapter A by merely providing as shown in FIG. 6 one or two tubular connections k similar to connector k and attaching a conduit f thereto and pushing them into bores 22*b* and 24*b* and connecting it directly to at least one or both of the valve bodies 18*b* and 20*b* of the sampling device 12*b*. The needle of a syringe may then be inserted into either one of the retainers 46*b* to pierce the septum 44*b* and thereby withdraw fluid for analysis.

We claim:

1. A device for taking a preserving a fluid sample for analysis comprising:

a tubular body including an outer wall extending around an inner chamber; opposite inlet and outlet end portions sealingly attached to and extending from opposite ends of the outer wall and having inlet and outlet passages extending therethrough to the inner chamber;

gas tight valve means in the inlet and outlet end portions for selectively allowing and preventing the flow of fluid through the inlet and outlet passages and into and out of the inner chamber;

an access passage into the inner chamber positioned in between the gas tight valve means;

seal means including a self sealing septum adjacent the inner chamber for sealing off the access passage to the inner chamber and which functions as a port for withdrawing a sample of the fluid sealed within the inner chamber for analysis by means of sealably inserting a hypodermic needle of any suitable device through the septum; and fastening means on both the inlet and outlet end portions for selectively connecting additional attachments or adapters and another of the said device thereto.

2. A device according to claim 1 further comprising:
   an inlet check valve unit sealingly connected to the fastening means on the inlet end portion of the tubular body for preventing escape from the inner chamber of a fluid sample taken therein from a body of fluid.

3. A device according to claim 2 further comprising:
   an outlet extension unit connected to the fastening means on the outlet end portion of the tubular body for providing a vent and allowing the fluid to completely fill the inner chamber and overflow into the outlet extension unit.

4. A device according to claim 1 wherein each of the gas tight valve means comprises:
   a valve stem rotatably mounted in and sealingly engaging a mating bore in each of the inlet and outlet end portions and having a valve bore rotatable into and out of alignment with the inlet and outlet passage, and actuating means on an end of the valve stem for manually rotating the valve stem and valve bore into and out of alignment with the inlet and outlet passages.

5. A device according to claim 4 wherein the gas tight valve means comprises:
   a tapered valve stem rotatably mounted in and sealingly engaging a mating tapered bore in each of the inlet and outlet end portions.

6. A device according to claim 1 wherein the seal means and septum is located in the outer wall adjacent the inner chamber and between the gas tight valve means.

7. A device according to claim 1 wherein the seal means including the septum is situated in one of the inlet and outlet end portions and adjacent the inner chamber and between the gas tight valve means.

8. A device according to claim 1 wherein the seal means including the septum is located in each of the inlet and outlet end portions and adjacent the inner chamber and between the gas tight valve means.

9. A device according to claim 2 wherein the inlet check valve unit comprises:
   a valve body extending between upper and lower ends thereof having an inner wall extending around a valve chamber and downwardly from the upper end to a valve seat;
   a valve inlet passage extending from the valve seat to the lower end; and
   a freely movable check valve adapted to sealingly engage the valve seat about the valve inlet and prevent fluid above the check valve from escaping out through the valve inlet passage.

10. A device according to claim 3 wherein the outlet extension means comprises:
    a hollow extension body with an upper and a lower end having an external wall extending about an inner cavity and axially between upper and lower ends thereof, attaching means on the lower end of the external wall for engaging the fastening means on the outlet end portion of the tubular body, and support means attached to the upper end of the external wall for lowering and raising the device respectfully into and out of a body of fluid to be tested.

11. A device according to claim 1 wherein at least the outer wall around the inner chamber is made from a transparent material.

12. A device according to claim 1 wherein the fastening means comprises:
    a threaded end portion on each of the inlet and outlet end portions.

13. A device according to claim 1 wherein each of the inlet and outlet end portions comprises:

a valve body sealingly connected to the opposite ends of the outer wall of the tubular body.

14. A device according to claim 1 wherein the device further comprises:

another of the said device coupled to the fastening means of the device for simultaneously taking and preserving more than one fluid sample taken from a body of fluid.

15. A device according to claim 1 wherein the fastening means comprises:

a counter bore and surface situated adjacent to and about inlet and outlet ends of the inlet and outlet passages in the inlet and outlet end portions and adapted for sealing engagement with surfaces of a tubular connecting portion of another device or accessory adapted for attachment thereto.

* * * * *